United States Patent [19]

Marynowski et al.

[11] 4,337,213

[45] Jun. 29, 1982

[54] CONTROLLED CRYSTALLIZATION DIPEROXYACID PROCESS

[75] Inventors: Chester W. Marynowski, Mountain View; Maria A. Geigel, Menlo Park, both of Calif.

[73] Assignee: The Clorox Company, Oakland, Calif.

[21] Appl. No.: 226,241

[22] Filed: Jan. 19, 1981

[51] Int. Cl.$^3$ .......................................... C07C 179/15
[52] U.S. Cl. ............................ 260/502 R; 568/566
[58] Field of Search ................. 568/566; 260/502 R, 260/502

[56] References Cited

U.S. PATENT DOCUMENTS

| | | | |
|---|---|---|---|
| 2,813,885 | 11/1957 | Swern et al. | 260/406 |
| 2,813,896 | 11/1957 | Krimm | 260/502 |
| 3,547,595 | 12/1970 | Olivier et al. | 23/295 |
| 3,547,597 | 12/1970 | Hays | 23/302 |
| 3,879,173 | 4/1975 | de Vries et al. | 23/301 |
| 3,880,914 | 4/1975 | Nielsen | 260/502 |
| 3,900,292 | 8/1975 | Fairchild | 23/273 |
| 3,996,152 | 12/1976 | Edwards et al. | 252/186 |
| 4,119,660 | 10/1978 | Hutchins | 260/502 |
| 4,233,235 | 11/1980 | Camden et al. | 260/502 R |
| 4,244,884 | 1/1981 | Hutvhins et al. | 260/502 R |

FOREIGN PATENT DOCUMENTS 970 3/1979 European Pat. Off. .............. 179/10

OTHER PUBLICATIONS

W. E. Parker, Journal of the American Chemical Society, Apr. 1957, p. 1929.

Organic Peroxides, vol. 1, Daniel Swern Editor, May 1970, p. 388.

Primary Examiner—Werren B. Lone
Attorney, Agent, or Firm—Phillips, Moore, Lempio & Majestic

[57] ABSTRACT

Diperoxyacids are unstable compounds, and processes for their production have normally provided relatively low product throughputs per reactor vessel volume. The present invention is a method for making diperoxyacids in which formation of the diperoxyacids is controlled and a high solids throughput may be achieved. The inventive method includes a controlling step wherein a reaction solids phase is maintained at not greater than about 36 wt. % of a reaction system, more preferably maintained at about 12 wt. % to about 36 wt. %.

19 Claims, No Drawings

CONTROLLED CRYSTALLIZATION DIPEROXYACID PROCESS

DESCRIPTION

1. Technical Field

The present invention relates to a process for making diperoxyacids, and particularly to a diperoxyacid process in which crystal formation of the diperoxyacid is controlled and a high solids throughput may be achieved.

2. Background Art

Peroxy compounds are effective bleaching agents, and compositions including diperoxyacid compounds have been disclosed as useful for industrial or home laundering operations. For example, U.S. Pat. No. 3,996,152, issued Dec. 7, 1976, inventors James B. Edwards et al, discloses bleaching compositions including peroxygen compounds such as diperazelaic acid and diperisophthalic acid.

For certain types of fabrics and dyed articles a bleaching solution including one or more diperoxyacids may be preferable rather than use of a bleaching solution including hypochlorite. Additionally, bleaching compositions including diperoxyacids can be packaged and stored as granular products which, when utilized in laundering operations, are automatically diluted before coming in contact with fabrics.

Early, laboratory preparations for diperoxyacids were disclosed by Parker, et al, *Journal of the American Chemical Society*, Volume 79, pages 1929-1931 (1957), in U.S. Pat. No. 2,813,896, issued Nov. 19, 1957, inventor Heinrich Krimm and in U.S. Pat. No. 2,813,885, issued Nov. 19, 1957, inventor Daniel Swern. These reported the production of aliphatic diperoxyacids in good yield.

However, the large scale, commercial production of diperoxyacids has incurred serious safety hazards. Such hazards have been at least partially overcome, but to the detriment of solids throughput and production costs. The safety problem is primarily due to the fact that diperoxyacids are unstable. Thus, a slurry of the diperoxyacid crystals formed and forming within a reaction vessel, if exposed to "hot spots", can experience spontaneous decomposition of the diperoxyacid. Production costs have tended to be high, partly due to the relatively low quantity of product throughput per reactor vessel volume which has been utilized by the prior art processes.

U.S. Pat. No. 4,119,660, issued Oct. 10, 1978, inventor James P. Hutchins, discloses a batch diperoxyacid process in which the liquid reaction components (hydrogen peroxide, water and sulfuric acid) are mixed, and then an aliphatic, dibasic carboxylic acid is added slowly. This mixture is maintained at a relatively low temperature until the diperoxyacid crystals are formed. However, the process is not very efficient for large scale, commercial production.

Another approach is disclosed by European patent application No. 78200149.9, published Mar. 7, 1979, inventors Camden et al, which discloses a continuous process for making aliphatic diperoxyacids. Inlet flow rates to the reactor are sufficient to maintain the liquid components thereof within specified ranges. This publication suggests that the diperoxyacid process can be seeded with crystals of diperoxyacid to yield larger, more easily filtered crystals of the resultant diperoxyacid product.

However, simply maintaining the liquid concentration within a reactor vessel during production of diperoxyacids is not adequate to prevent the tendency of spontaneous nucleation and formation of unpumpable slurry and potential thermal decomposition, particularly if the reaction solids mass were to exceed about 7 to 10 weight percent of the total reaction system.

Alternatively, where the reaction solids mass within the reactor vessel (and hence the product throughput ultimately obtainable) is less than about 7 to 10 weight percent of the reaction system, then the slurry of diperoxyacid product tends to be very watery, and the overall productivity, or product throughput, tends to be low.

DISCLOSURE OF THE INVENTION

The present invention is directed to overcoming one or more of the problems as set forth above.

In one aspect of this invention, a method of making a diperoxyacid product comprises the steps of providing a two-phase initial system in a reaction vessel, feeding a dicarboxylic acid component into the two-phase initial system to form a reaction system, and controlling a rate of the dicarboxylic acid component fed at a selected value. The selected value is determined from a surface area of a reaction solids phase within the vessel. The feeding step also includes feeding sulfuric acid, hydrogen peroxide and water components into the vessel, and controlling the components being fed to maintain the reaction solids phase at not greater than about 36 weight percent, preferably to within a range of from about 12 wt. % to about 36 wt. %, of the reaction system.

The present invention utilizes minimum amounts of components, provides safe, economical production of diperoxyacids having a relatively large crystal size, and may be practiced either by batches or in a continuous-flow mode. A particularly desirable result of the present invention is the ability to operate with large quantities of reaction solids, which are easily pumped and separated from the reaction system, to yield a high productivity per reactor vessel volume.

BEST MODE OF CARRYING OUT THE INVENTION

The present invention is a method for making diperoxyacids, and particularly diperoxyacids of the formula

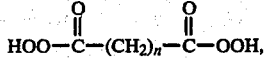

wherein n is about 4 to about 18. Preferred diperoxyacids made in accordance with the present invention are wherein n=7 to 12; particularly preferred diperoxyacids made in accordance with the invention are diperoxyazelaic acid and diperoxydodecanedioic acid.

Broadly, the method of the present invention involves providing in a reaction vessel a liquid and a solid which form a two-phase initial system. A dicarboxylic acid is fed into the two-phase initial system to form a reaction system. This reaction system includes a reaction solids phase. The reaction solids phase comprises the solid from the two-phase initial system and the diperoxyacid product which results from peroxidation of the dicarboxylic acid fed.

Additional feed components include sulfuric acid, hydrogen peroxide, and water. The individual feed components may be added singly or as mixtures formed from commercially available grades of chemicals; however, these components are fed at controlled rates which are, in the preferred aspect of the inventive method, determined by a plurality of criteria. The components are preferably fed by various conventional means such as, for example, metering pumps.

Generally, and as more particularly discussed hereinafter, these criteria are as follows: the dicarboxylic acid feed rate is determined by a surface area of the reaction solids phase; the hydrogen peroxide feed rate is preferably determined by a selected mole ratio of hydrogen peroxide to dicarboxylic acid; the sulfuric acid feed rate is preferably determined by a selected value of an oxidizing index of the reaction system (hereafter referred to as $I_o$); and, the water feed rate is preferably determined by a selected value of a hydration index of the reaction system (hereinafter referred to as $I_H$).

These criteria, and the steps of the inventive method, shall now be more fully described.

Providing Step

The present invention may be practiced in various, conventional reaction vessels, such as a reaction vessel equipped with means for monitoring temperature, means for internal stirring, and means for cooling. Preferred materials for the vessel's inner surface are preferably glass, porcelain, and polytetrafluoroethylene. Where the invention is practiced in a continuous-flow mode, a series array of reactors may be utilized to attain a close approach to complete conversion and crystallization.

A liquid and a solid are provided within the reaction vessel to form the two-phase initial system. The liquid includes hydrogen peroxide, sulfuric acid and water in proportions which result in a liquid composition predicted from the chosen reaction stoichiometry.

Preferably, the liquid of the two-phase initial system is from about 0.1 wt. % to about 30 wt. % hydrogen peroxide, from about 30 wt. % to about 85 wt. % sulfuric acid, and from about 10 wt. % to about 50 wt. % water.

The solid of the providing step is preferably in crystalline form in a size range of from about 1 to about 25 microns. The quantity of crystalline solid in the two-phase initial system should be sufficient to bring the concentration of undissolved "seed crystals" in the range of from about 0.01 wt. % to about 34 wt. % of the two-phase initial system, more preferably from about 0.1 wt. % to about 10 wt. %, most preferably from about 0.2 wt. % to about 2 wt. %.

The solid of this two-phase initial system is a diperoxyacid, preferably having from about 6 to about 20 carbon atoms (e.g. n is about 4 to about 18). The solid may be added batchwise to the liquid in a form of dry, crystalline diperoxyacid, or as a slurry (containing one or more of the components of the two-phase initial system liquid). It is immaterial whether the diperoxyacid is added as a solid or as a slurry, and either form is suitable for the providing step of the inventive method.

The total volume of the two-phase initial system should be adequate to permit sufficient mixing and cooling throughout the next-described feeding step. Such cooling is well known to the art, and preferably maintains the reactants in the range of about 0° C. to about 60° C., more preferably from about 15° C. to about 50° C. during the reaction.

Feeding Step

The principal feed component is a dicarboxylic acid, preferably having from about 6 to about 20 carbon atoms, e.g. chosen from dicarboxylic acids of the formula

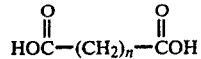

(wherein n is about 4 to about 18), which is fed into the two-phase initial system, is peroxidized, and forms diperoxyacid product in the reaction system. More preferred dicarboxylic acid feed components are wherein n=7 to 12; most preferred dicarboxylic acids are azelaic acid and dodecanedioic acid.

The feeding step also includes feeding sulfuric acid, hydrogen peroxide and water components. These four feed components may be added singly or as mixtures, and may be added continuously or in increments spaced at convenient, relatively short intervals, for example about five minutes apart. However, whether a continuous feed of the components or an incremental feed is chosen, the feed rates are controlled so as to control the crystallization of diperoxyacid product. The dicarboxylic acid is preferably fed as a solution in the sulfuric acid component.

The reaction system comprises a reaction liquid phase and a reaction solids phase. (A minor gaseous phase of oxygen, formed in side reactions, is normally also present in the reaction system.) The reaction solids phase includes the solid, diperoxyacid seed crystals and the diperoxyacid product which forms substantially thereupon. The reaction solids phase is in the form of a slurry which, in conjunction with the controlling step, is maintained at not greater than 36 wt. % of the two-phase reaction system during practice of the present invention.

The initial seed crystals of the providing step assist in controlling (e.g. tend to maximize) the crystal size of the diperoxyacid product, and also assist in preventing the slurry from becoming thixotropic.

Controlling Step

The overall controlling of components being fed during the feeding step maintains the reaction solids phase at not greater than about 36 wt. % of the reaction system. Above about 36 wt. %, the reaction system becomes so viscous as to be difficult to stir.

More preferably, the controlling step maintains the reaction solids phase at a selected value from about 12 wt. % to about 36 wt. % of the reaction system. Below about 12 wt. %, the slurry is relatively watery and the productivity of the reactor is relatively low. Control of each component shall now be more particularly described.

(1) Dicarboxylic Acid Control

The dicarboxylic acid being fed in the feeding step is controlled at a selected feed rate which is determined by a surface area. More particularly, the surface area is that of the exposed, diperoxyacid crystals present in the reaction vessel at that time.

Thus, for example, prior to having fed any dicarboxylic acid, the initial surface area will substantially be the solid diperoxyacid seed crystals which, along with the liquid, form the two-phase initial system. The initial surface area of the dicarboxylic acid may be, and preferably is, experimentally determined by withdrawing a small sample of the two-phase initial system from the reaction vessel, placing an aliquot of this sample under a microscope, measuring the average size of undissolved diperoxyacid crystals, separately determining the mass concentration of solids in the sample by filtering, drying, and weighing the solids from a measured aliquot, and calculating the surface area present in the two-phase initial system. For example, an area calculation may be as follows:

$$m^2 = (g) \times \left(\frac{\mu m^2}{\mu m^3}\right) \times \left(\frac{\mu m}{cm}\right)^3 \times \left(\frac{cm^3}{g}\right) \times \left(\frac{m}{\mu m}\right)^2$$

$$= (W) \times \left(\frac{6D_M^2}{D_M^3}\right) \times \left(\frac{10^4}{1}\right)^3 \times \left(\frac{1}{1.2}\right) \times \left(\frac{10^{-6}}{1}\right)^2$$

$$= 5 \, W/D_M; \begin{pmatrix} W = \text{wt. of undissolved seed, g;} \\ D_M = \text{average median diameter*, } \mu m. \end{pmatrix}$$

*(This assumes that the crystals are rectangular solids whose area is equal to that of a cube of the same $D_M$.)

As the dicarboxylic acid (and other components) are fed, and with negligible attrition of product crystals, the total available surface area of the reaction solids phase in the reaction system increases roughly as the ⅔ power of the reaction solids phase mass. Thus, if the dicarboxylic acid is being fed by increments, each successive increment can be calculated in relation to the first fed increment. Such a calculated, successive addition schedule is specific for a given mass of solid in the two-phase initial system and for a given initial median particle size of the solid.

As an alternative (or in addition) to such an extrapolated determination of the surface area, as the reaction progresses the surface area may be empirically determined by periodically taking samples and performing the microscopic examination and calculation described above.

In the best mode contemplated for practice of the present invention, an initial solid surface area is determined for a particular mass of diperoxyacid solid in the two-phase initial system and for a particular particle size of this solid. Then as the reaction proceeds, periodic determinations are made of the exposed diperoxyacid crystal surface area present in the reaction vessel. These determinations may then be plotted as a function of time. The graphical data may then be utilized to determine the particular, desired value selected for the dicarboxylic acid component feed rate. It has been found that, for optimum crystal growth, the preferred value of the feed rate of the dicarboxylic acid component lies between about 0.1 to about 100 grams per hour per square meter of reaction solids surface area present. Where the inventive method is being practiced for making diperoxyazelaic acid, the selected value of dicarboxylic acid component (e.g. azelaic acid) is preferably between about 1 and about 10 grams per hour per square meter of reaction solid phase surface area.

(2) Hydrogen Peroxide Control

The hydrogen peroxide feed rate at any given moment is controlled to maintain a defined mole ratio at a selected value between about 1 and about 40. This mole ratio is defined by the cumulative amount of hydrogen peroxide which has been fed to the cumulative amount of dicarboxylic acid which has been fed. (By cumulative is meant the total amount of the component fed into the reaction vessel at that point of time.) In the preferred practice of the invention method, this mole ratio of the cumulative amount of hydrogen peroxide to the cumulative amount of dicarboxylic acid is preferably maintained at a selected value between about 2 and about 10.

(3) Sulfuric Acid Control

The sulfuric acid feed rate at any given moment is preferably controlled to maintain an oxidizing index, or $I_O$, of the liquid phase of the reaction system at a selected value, preferably between about 0.01 and about 10. This $I_O$ is defined as the ratio of two molar sums, as illustrated by the following equation:

$$I_O = \frac{(\text{moles of } H_2O_2 + \text{moles of } H_2SO_5)}{(\text{moles of } H_2SO_4 + \text{moles of } H_2SO_5)}$$

In the above equation the numerator represents the sum of the moles of hydrogen peroxide and the moles of persulfuric acid present in the reaction system at that moment; the denominator represents the sum of the moles of sulfuric acid and the moles of persulfuric acid present in the reaction system at that moment. Persulfuric acid (Caro's acid) is included in the definition of $I_O$ to allow for the fact that part of the hydrogen peroxide and part of the sulfuric acid are reversibly converted to persulfuric acid in the reaction system. When the present invention is practiced for making diperoxyazelaic acid, the $I_O$ of the reaction system is most preferably maintained at a selected value between about 0.1 to about 1.

The quantities of hydrogen peroxide, sulfuric acid and persulfuric acid at any particular moment are preferably determined by periodically taking a sample of the reaction mixture within the reaction vessel and determining the moles of hydrogen peroxide, sulfuric acid and persulfuric acid by conventional analytical procedures. The $I_O$ for the reaction mixture is then calculated from the above formula, and the amount of sulfuric acid being fed is selectively adjusted to maintain the $I_O$ at a selected value within the range between about 0.1 and about 10, more preferably from about 0.1 and about 1.

In the best mode contemplated for practice of the present invention, the $I_O$ is determined in the two-phase initial system and periodically determined thereafter in the reaction system at about 10 or 15 minute intervals. For subsequent runs the data obtained from such determinations may be graphically plotted, and the sulfuric acid feed rate controlled in accordance with the graphs.

(4) Water Control

The water feed rate at any given moment is preferably controlled to maintain a defined quantity designated as the hydration index, or $I_H$, of the reaction system. The $I_H$ is maintained at a selected value in the range between about 0.5 and about 10. The hydration index is defined by the following equation:

$$I_H = \frac{\text{moles of } H_2O}{(\text{moles of } H_2SO_4 + \text{moles of } H_2SO_5)}$$

That is, $I_H$ is defined as the ratio whose numerator represents the moles of water in the reaction system at that moment, and whose denominator is identical with the denominator of $I_O$. When diperoxyazelaic acid is being made in accordance with the present invention, the $I_H$ is most preferably maintained at a selected value in the range between about 1.5 and about 3.

In the best mode contemplated for the present invention, the $I_H$ is periodically determined and graphically plotted in a manner analogous to that described above for the $I_O$. Subsequent runs may then be controlled in accordance with the graphs.

Practice of the present invention will now be illustrated by the following Examples (I-VI), below.

EXAMPLE I

A pilot plant run was made in accordance with the present invention wherein the reaction solids phase was maintained at about 22 wt. % of the reaction system, the selected value of $I_O$ was 0.33, and the selected value of $I_H$ was 2.4. The duration of this run was 396 minutes. Data from this run are summarized in Table I, below.

The Example I run gave an excellent yield (95.8%) and conversion (93.0%) of diperoxyazelaic acid (DPAA) from azelaic acid (AA). The diperoxyazelaic acid product therefrom was separated by filtration and recovered as crystalline product having a particle size between about 5 and about 40 microns.

EXAMPLE II

Another pilot plant run was conducted in accordance with the present invention wherein the reaction solids phase was maintained at about 26 wt. % of the reaction system. $I_O$ was maintained at a value of 0.35 and $I_H$ was maintained at 2.41. Data from this run are summarized in Table II.

TABLE II

| | | Summary Data | | | | | |
|---|---|---|---|---|---|---|---|
| Run Descriptor | Units | Total Stream | AA | $H_2SO_4$ | $H_2O_2$ | $H_2O$ | DPAA |
| Seed Composition | Grams | 1652 | 12 | ND | ND | ND | 347 |
| Net amount fed* | Gram moles | | 95.0 | 350.3 | 292.8 | 632.6 | 0 |
| Net amount recovered* | Gram moles | | 3.2 | | | | 84.9 |
| Yield (from unrecovered AA) | Mole percent | | | | | | 92.4 |
| Conversion (from fed AA) | Mole percent | | | | | | 89.3 |
| Actual feed ratio (based on AA) | Moles/mole | | 1 | 3.69 | 3.08 | 6.66 | |
| Target feed ratio (based on AA) | Moles/mole | | 1 | 3.67 | 3.00 | 6.50 | |
| Actual feed rate (average) | Gram moles/minute | | 0.241 | | | | |
| Target feed rate | Gram moles/minute | | >>0.103** | | | | |

*In continuous operation, excluding seed slurry and wash water
**In this run there was no fixed target feed rate for AA; instead, the goal was to increase the feed rate gradually throughout the run in proportion to the increasing available crystal surface, so as to determine the maximum productivity of the reactor. (The target feed ratio listed was only for initiation of the run.)
ND = Not Determined Duration of the run summarized by Table II was 394 minutes. Yield (92.4%) and conversion (89.3%) were slightly lower than of the Example I run. The resultant product crystals were about 15-20 microns. The final, unwashed filter cake had an indicated average solids content of about 36.1%.

EXAMPLE III

Another run was performed wherein the reaction solids phase was maintained at about 13 wt. % of the reaction system. $I_O$ was maintained at 1.92 and $I_H$ was maintained at 5.85. Duration of the run was 326 minutes.

TABLE I

| | | Summary Data | | | | | |
|---|---|---|---|---|---|---|---|
| Run Descriptor | Units | Total Stream | AA | $H_2SO_4$ | $H_2O_2$ | $H_2O$ | DPAA |
| Seed Composition | Grams | 7203 | 5 | 972 | 136 | 387 | 255 |
| Net amount fed* | Gram moles | | 54.0 | 198.4 | 165.5 | 357.6 | 0 |
| Net amount recovered* | Gram moles | | 1.6 | | | | 50.2 |
| Yield (from unrecovered AA) | Mole percent | | | | | | 95.8 |
| Conversion (from fed AA) | Mole percent | | | | | | 93.0 |
| Actual feed ratio (based on AA) | Moles/mole | | 1 | 3.67 | 3.06 | 6.62 | |
| Target feed ratio (based on AA) | Moles/mole | | 1 | 3.67 | 3 | 6.50 | |
| Actual feed rate | Gram moles/minute | | 0.136 | | | | |
| Target feed rate | Gram moles/minute | | 0.137 | | | | |

*In continuous operation, excluding wash water and starting mix.

Data from this run are summarized in Table III

TABLE III

| | | Summary Data | | | | | |
|---|---|---|---|---|---|---|---|
| Run Descriptor | Units | Total Stream | AA | $H_2SO_4$ | $H_2O_2$ | $H_2O$ | DPAA |
| Seed Composition | Grams | 1450 | 9 | ND | ND | ND | 275 |
| Net amount fed* | Gram moles | | 33.1 | 99.1 | 268.7 | 497.2 | 0 |
| Net amount recovered* | Gram moles | | 1.5 | | | | 30.0 |
| Yield (from unrecovered AA) | Mole percent | | | | | | 94.9 |
| Conversion (from fed AA) | Mole percent | | | | | | 90.6 |
| Actual feed ratio (based on AA) | Moles/mole | | 1 | 2.99 | 8.12 | 15.02 | |

TABLE III-continued

| Run Descriptor | Units | Summary Data Total Stream | AA | H₂SO₄ | H₂O₂ | H₂O | DPAA |
|---|---|---|---|---|---|---|---|
| Target feed ratio (based on AA) | Moles/mole | | 1 | 3 | 8 | 14.8 | |
| Actual feed rate | Gram moles/minute | | 0.102 | | | | |
| Target feed rate | Gram moles/minute | | 0.108 | | | | |

*In continuous operation, excluding seed slurry and wash water
ND = Not Determined Conversion (90.6%) and yield (94.9%) were excellent; however, the resultant product crystals tended to be relatively small (about 5 microns), the final unwashed filter cake had an indicated average solids content of about 24%, and filterability was relatively slow. It is believed that these less favorable crystallization results are primarily attributable to the relatively high $I_H$ value.

EXAMPLE IV

Another pilot plant run was conducted wherein the reaction solids phase was maintained at about 15 wt. %. The $I_O$ was maintained at 0.12 and the $I_H$ was maintained at 1.73. Duration of this run was 340 minutes. Data is summarized in Table IV.

TABLE IV

| Run Descriptor | Units | Summary Data Total Stream | AA | H₂SO₄ | H₂O₂ | H₂O | DPAA |
|---|---|---|---|---|---|---|---|
| Seed Composition | Grams | 1846 | 12 | ND | ND | ND | 412 |
| Net amount fed* | Gram moles | | 52.6 | 173.9 | 101.3 | 211.2 | 0 |
| Net amount recovered* | Gram moles | | 2.2 | | | | 40.9 |
| Yield (from unrecovered AA) | Mole percent | | | | | | 81.2 |
| Conversion (from fed AA) | Mole percent | | | | | | 77.8 |
| Actual feed ratio (based on AA) | Moles/mole | | 1 | 3.31 | 1.93 | 4.02 | |
| Target feed ratio (based on AA) | Moles/mole | | 1 | 3.3 | 2 | 4.15 | |
| Actual feed rate | Gram moles/minute | | 0.155 | | | | |
| Target feed rate | Gram moles/minute | | 0.15 | | | | |

*In continuous operation, excluding seed slurry and wash water
ND = NOT DETERMINED This run gave a yield of 81.2% and a conversion of 77.8%. The final unwashed filter cake had an indicated average solids content of 28.5%. The product crystals were relatively large (10-20 microns), which filtered very quickly.

EXAMPLE V

Another run was made wherein the reaction solids phase was maintained at about 9 wt. %. The $I_O$ was 1.38 and the $I_H$ was 6.11. Duration of this run was 420 minutes. The data is summarized in Table V.

TABLE V

| Run Descriptor | Units | Summary Data Total Stream | AA | H₂SO₄ | H₂O₂ | H₂O | DPAA |
|---|---|---|---|---|---|---|---|
| Seed Composition | Grams | 1478 | 10 | ND | ND | ND | 330 |
| Net amount fed* | Gram moles | | 22.1 | 51.2 | 133.7 | 24.7 | 0 |
| Net amount recovered* | Gram moles | | 1.4 | | | | 19.3 |
| Yield (from unrecovered AA) | Mole percent | | | | | | 92.8 |
| Conversion (from fed AA) | Mole percent | | | | | | 86.9 |
| Actual feed ratio (based on AA) | Moles/mole | | 1 | 2.31 | 6.02 | 11.16 | |
| Target feed ratio (based on AA) | Moles/mole | | 1 | 2.3 | 6 | 11.1 | |
| Actual feed rate | Gram moles/minute | | 0.053 | | | | |
| Target feed rate | Gram moles/minute | | 0.061 | | | | |

*In continuous operation, excluding seed slurry and wash water
ND = Not Determined Yield was 92.8% and conversion 86.9%. The final unwashed filter cake had an indicated average solids content of 24.1%. However, the product crystals tended to be small (about 2-3 microns), which filtered and washed very slowly. As in the run illustrated by Example III, above, the $I_H$ was relatively high.

EXAMPLE VI

Another pilot plant run was made wherein the reaction solids phase was maintained at about 15 wt. %. The $I_O$ was 0.31 and the $I_H$ was 1.65. Duration of this run was 285 minutes. The data is summarized in Table VI.

TABLE VI

| Run Descriptor | Units | Summary Data Total Stream | DDA | H₂SO₄ | H₂O₂ | H₂O | DPDDA |
|---|---|---|---|---|---|---|---|
| Seed composition | Grams | 1300 | 3 | ND | ND | ND | 101 |
| Net amount fed* | Gram moles | | 21.9 | 219 | 116.3 | 280.5 | 0 |
| Yield (from unrecovered DDA) | Mole percent | | | | | | 93.2 |
| Conversion (from fed DDA) | Mole percent | | | | | | 88.1 |

TABLE VI-continued

| | | Summary Data | | | | | |
|---|---|---|---|---|---|---|---|
| Run Descriptor | Units | Total Stream | DDA | $H_2SO_4$ | $H_2O_2$ | $H_2O$ | DPDDA |
| Actual feed ratio (based on DDA) | Moles/mole | | 1 | 10.0 | 5.3 | 12.8 | |
| Target feed ratio (based on DDA) | Moles/mole | | 1 | 10.0 | 5.4 | 12.9 | |

*In continuous operation, excluding wash water and seed slurry
ND = Not Determined Yield of diperoxydodecanedioic acid (DPDDA) was 93.2% and conversion from dodecanedioic acid (DDA) was 88.1%. The final unwashed filter cake had an indicated average solids content of 46.6%. The product crystals were about 5–30 microns.

As has been previously noted, the present invention may be practiced either in batches or in continuous-flow. Where the process is batch, the total multi-phase reaction system at the conclusion of the reaction is preferably transferred to a filter or other conventional separation device and the diperoxyacid product crystals are separated. Where the process is continuous-flow, the reaction system is preferably being withdrawn, normally continuously, from the reactor during the feeding step at a rate sufficient to maintain a substantially constant reaction system volume in the reactor.

The reaction liquid phase remaining after these separations may optionally be recycled. For example, this reaction liquid phase (from which the reaction solids phase has been separated) may be utilized as at least a portion of the liquid of the providing step. Also, this reaction liquid phase, having the reaction solids phase separated therefrom, may be fed into the reactor during the feeding step in order to assist in maintaining the reaction solids phase at the preferred wt. % of the reaction system.

The separated reaction solids phase (e.g. the diperoxyacid product crystals) may then be washed with water and dried by various conventional techniques while observing the usual safeguards for handling peroxy acids.

INDUSTRIAL APPLICABILITY

The inventive method is preferably operated at a reaction solids phase content of from about 12 wt. % to about 36 wt. %. Such a high solids content slurry minimizes the size of the reaction vessels required, and the high filterability of the slurry at preferred operating conditions minimizes the size of filtration equipment required to produce high solids content filter cakes.

The inventive method is preferably utilized for making peracids for commercial organic peroxygen bleaching agents. The diperoxyacid product made in accordance with the inventive method, and compositions such as those including detergents, can be packaged and stored as granular products for use in laundering operations.

Other aspects, objects and advantages of this invention can be obtained from a study of the disclosure and the appended claims.

We claim:

1. A method for making a diperoxyacid product comprising the steps of:
   providing a liquid and a solid, said liquid and said solid forming a two-phase initial system, said liquid including hydrogen peroxide, sulfuric acid and water, said solid being a diperoxyacid, said solid being in an amount of from about 0.01 wt. % to about 34 wt. % of said two-phase initial system;
   feeding a dicarboxylic acid component, a sulfuric acid component, a hydrogen peroxide component, and a water component into said two-phase initial system to form a reaction system, said dicarboxylic acid component being of the formula

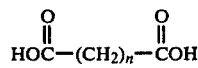

wherein n is about 4 to about 18, said reaction system including a reaction solids phase, said reaction solids phase including said solid of said two-phase initial system and diperoxyacid product;
   controlling said components being fed during the feeding step to maintain said reaction solids phase at not greater than about 36 wt. % of said reaction system, the controlling including determining a surface area of said reaction solids phase and maintaining a feed rate of said dicarboxylic acid component at a selected value between about 0.1 and about 100 grams per hour per square meter of said surface area.

2. The method as in claim 1 wherein said liquid of said two-phase initial system has from about 0.1 wt % to about 30 wt. % $H_2O_2$, from about 30 wt. % to about 85 wt. % $H_2SO_4$, and from about 10 wt. % to about 50 wt. % $H_2O$ therein, and said solid is in an amount of from about 0.1 wt. % to about 10 wt. %.

3. The method as in claim 1 wherein said diperoxyacid of the providing step is of the formula

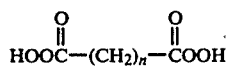

wherein n is about 4 to about 18.

4. The method as in claim 2 wherein said selected value of said dicarboxylic acid component is between about 1 and about 10 grams per hour per square meter of said surface area.

5. The method as in claim 1 wherein the controlling step maintains said reaction solids phase within a range of from about 12 wt. % to about 36 wt. % of said reaction system.

6. The method as in claim 1 wherein the controlling step includes determining a cumulative amount of said $H_2O_2$ and a cumulative amount of said dicarboxylic acid fed and maintaining a mole ratio of said cumulative amount of said $H_2O_2$ to said cumulative amount of said dicarboxylic acid at a selected value.

7. The method as in claim 6 wherein said selected value of said mole ratio is within a range of from about 1 and about 40.

8. The method as in claim 1 wherein the controlling step includes determining an index $I_o$ of said two-phase reaction system, said index $I_o$ defined by the formula $$(\text{moles of } H_2O_2 + \text{moles of } H_2SO_5)/(\text{moles of } H_2SO_4 + \text{moles of } H_2SO_5),$$

said $H_2SO_5$ being reversibly formable by reaction of said $H_2O_2$ and said $H_2SO_4$, and maintaining said $I_o$ at a selected value.

9. The method as in claim 8 wherein said selected value is between about 0.01 and about 10.

10. The method as in claim 8 wherein said selected value is between about 0.1 and about 1.

11. The method as in claim 4 wherein the controlling step includes determining on index $I_H$ of said reaction system, said index $I_H$ defined by the formula $$\text{moles of } H_2O/(\text{moles of } H_2SO_4 + \text{moles of } H_2SO_5),$$

said $H_2SO_5$ being reversibly formable by reaction of said $H_2O_2$ and said $H_2SO_4$, and maintaining said $I_H$ at a selected value.

12. The method as in claim 11 wherein said selected value is between about 0.5 and about 10.

13. The method as in claim 11 wherein said selected value is between about 1.5 and about 5.

14. The method as in claim 1 further comprising: separating said reaction solids phase from said reaction system.

15. The method as in claim 6 wherein said diperoxyacid is diperoxyazelaic acid, and said selected value of said mole ratio is within a range of about 1 and about 5.

16. The method as in claim 10 wherein said diperoxyacid is diperoxyazelaic acid.

17. The method as in claim 13 wherein said diperoxyacid is diperoxyazelaic acid.

18. The method as in claim 10 wherein said diperoxyacid is diperoxydodecanedioic acid.

19. The method as in claim 13 wherein said diperoxyacid is diperoxydodecanedioic acid.

* * * * *